US006548581B2

(12) United States Patent
Anderson et al.

(10) Patent No.: US 6,548,581 B2
(45) Date of Patent: Apr. 15, 2003

(54) ASYMMETRIC HALOGEN-ALKYL ALDITOL DERIVATIVES AS NUCLEATORS AND CLARIFIERS FOR POLYOLEFINS, AND POLYOLEFIN PLASTIC COMPOSITIONS CONTAINING SAME

(75) Inventors: John D. Anderson, Moore, SC (US); Darin L. Dotson, Spartanburg, SC (US); Jeffrey R. Jones, Inman, SC (US); Shawn R. Sheppard, Spartanburg, SC (US); Nathan A. Mehl, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 113 days.

(21) Appl. No.: 09/815,732

(22) Filed: Mar. 23, 2001

(65) Prior Publication Data

US 2003/0013786 A1 Jan. 16, 2003

(51) Int. Cl.[7] .............................. C08K 5/15; A61K 7/32; A61K 7/34; A61K 7/36
(52) U.S. Cl. ........................ 524/108; 524/297; 424/65; 424/66; 424/67; 424/68; 549/364
(58) Field of Search .................. 524/108, 297; 424/65, 66, 67, 68; 549/364

(56) References Cited

U.S. PATENT DOCUMENTS

| | | | |
|---|---|---|---|
| 3,721,682 A | 3/1973 | Murai et al. ............. 260/340.7 |
| 4,016,118 A | 4/1977 | Hamada et al. ...... 260/17.4 SG |
| 4,154,816 A | 5/1979 | Roehl et al. .................... 424/68 |
| 4,371,645 A | 2/1983 | Mahaffey, Jr. ............... 524/108 |
| 4,518,582 A | 5/1985 | Schamper et al. ............ 424/66 |
| 4,743,444 A | 5/1988 | McCall .......................... 424/65 |
| 4,781,917 A | 11/1988 | Luebbe et al. ................. 424/65 |
| 4,808,650 A | 2/1989 | Titus et al. ................... 524/108 |
| 4,816,261 A | 3/1989 | Luebbe et al. ................. 424/65 |
| 4,902,807 A | 2/1990 | Kobayashi et al. .......... 549/364 |
| 4,996,334 A | 2/1991 | Kaitoh et al. ................ 549/364 |
| 5,015,684 A | 5/1991 | Kobayashi et al. .......... 524/108 |
| 5,049,605 A | 9/1991 | Rekers ......................... 524/108 |
| 5,106,999 A | 4/1992 | Gardlik et al. .............. 549/364 |
| 5,470,898 A | 11/1995 | Syed ............................. 524/84 |
| 5,574,174 A | 11/1996 | Syed ............................ 549/364 |
| 5,609,855 A | 3/1997 | Oh et al. ........................ 424/65 |
| 5,696,186 A | 12/1997 | Videau ......................... 524/48 |
| 5,731,474 A | 3/1998 | Scrivens et al. ............. 568/592 |

FOREIGN PATENT DOCUMENTS

| | | |
|---|---|---|
| JP | [1990]-59832 | 12/1990 |
| JP | [1995]-286066 | 10/1995 |
| WO | 92/19221 | 11/1992 |

*Primary Examiner*—Kriellion A. Sanders
(74) *Attorney, Agent, or Firm*—Terry T. Moyer; William S. Parks

(57) ABSTRACT

This invention relates to plastic additives which are useful as nucleating agents and which are especially useful for improving the optical properties of polymeric materials. More particularly, this invention relates to certain bis-halogen-alkyl-benzylidene alditol acetals and polymer compositions thereof which are useful as materials for food or cosmetic containers and packaging. These bis-halogen-alkylbenzylidene alditol acetals are also useful as gelling agents for organic solvents, particularly those used in the preparation of antiperspirant gel sticks.

15 Claims, No Drawings

ASYMMETRIC HALOGEN-ALKYL ALDITOL DERIVATIVES AS NUCLEATORS AND CLARIFIERS FOR POLYOLEFINS, AND POLYOLEFIN PLASTIC COMPOSITIONS CONTAINING SAME

FIELD OF THE INVENTION

This invention relates to plastic additives which are useful as nucleating agents and which are especially useful for improving the optical properties of polymeric materials. More particularly, this invention relates to certain bis-halogen-alkyl-benzylidene alditol acetals and polymer compositions thereof which are useful as materials for food or cosmetic containers and packaging. These bis-halogen-alkylbenzylidene alditol acetals are also useful as gelling agents for organic solvents, particularly those used in the preparation of antiperspirant gel sticks.

BACKGROUND OF THE PRIOR ART

All U.S. Patents cited below are herein entirely incorporated by reference.

Numerous attempts have been made to improve the clarity and physical properties of polyolefins by incorporating certain kinds of additives in them. Applications such as the development of plates, sheets, films, containers, and syringes demand clarity or transparency as a necessary property. Commercially available additives fall into two categories termed "melt sensitive" and "melt insensitive". Melt sensitive additives have melting point which is below or near the normal processing temperatures of polyolefin based resins and include dibenzylidene sorbitol (DBS) systems. Melt insensitive additives do not melt at normal processing temperatures and include sodium benzoate and salts of organic phosphates as examples.

U.S. Pat. No. 4,016,118 to Hamada, et al. teaches that a polyolefin plastic composition containing 0.1% to 0.7% dibenzylidene sorbitol (DBS) as an additive will show improved transparency and reduced molding shrinkage over compositions containing a substituted benzoic acid salt. Additional advancements in sorbitol-based clarification technology have been driven by the need for improved transparency, reduction of plate-out during processing, and improved organoleptic properties. In order to overcome these deficiencies, many derivatives of DBS in which the aromatic rings are substituted with various groups have been proposed.

Mahaffey, in U.S. Pat. No. 4,371,645 discloses a series of dibenzylidene sorbitols having the general formula:

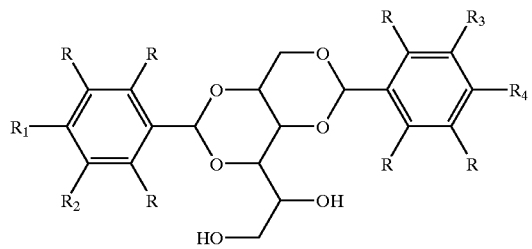

wherein R, $R_1$, $R_2$, $R_3$, and $R_4$, are selected from hydrogen, lower alkyl, hydroxy, methoxy, mono- and di-alkylamino, amino, nitro, and halogen, with the proviso that at least one of $R_1$, $R_2$, $R_3$, and $R_4$ is chlorine or bromine. Effective concentrations of the disclosed substituted DBS derivatives range from 0.01 to about 2 percent by weight of the total composition weight. Further improvements in transparency characteristics are disclosed by Titus, et al. in U.S. Pat. No. 4,808,650. In this patent mono and disubstituted DBS derivatives having the formula:

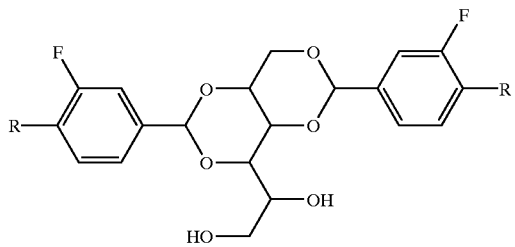

in which R may be hydrogen or fluorine provide improved clarity applications in polyolefins. Rekers, in U.S. Pat. No. 5,049,605 discloses a series of dibenzylidene sorbitols having the general formula:

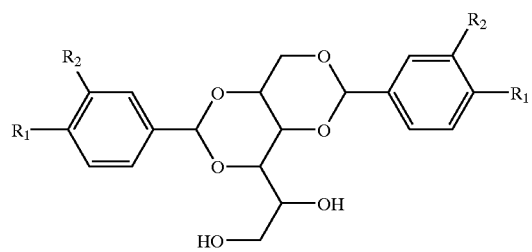

in which $R_1$ and $R_2$ are independently selected from lower alkyl groups containing 1–4 carbons which together form a carbocyclic ring containing up to 5 carbon atoms. Also disclosed are polyolefin plastics containing the above group of dibenzylidene sorbitols. This patent teaches that these compositions show improved transparency and improved organoleptic properties (desirable taste and odor characteristics) over previous "generations" of sorbitol-based clarifying agents. Videau, in U.S. Pat. No. 5,696,186 discloses substituted DBS derivatives with an alkyl group (methyl, ethyl, or the like) or halogen (fluorine, chlorine, or the like) on the benzene rings for use as nucleation/clarification agents in polyolefins.

Dibenzylidene sorbitol (DBS) derivatives that melt above 240° C. are generally recognized as being less soluble in polyolefins and thus require special processing to effect their dispersion into the polyolefin resin. Typically a higher molding temperature is used to dissolve the additive, but this can lead to decomposition of the additive as exhibited by plateout, yellowing of the resin, and odor generation. To overcome this limitation, mixtures of DBS systems have been used to effect nucleation of polyolefins at molding temperatures<240° C.

Japanese Patent No. 2[1990]-12259 discloses the use of asymmetric DBS systems derived from alkoxy and alkyl substituted benzaldehydes as nucleating agents for polyolefins. Japanese Patent No. 3[1991]-292383 discloses the use of asymmetric diacetals derived from a substituted benzaldehyde and aliphatic aldehydes as gelling agents and nucleating agents for polyolefin resins. U.S. Pat. No. 5,015,684 to Kobayashi, et al. teaches that an asymmetric DBS system derived from benzaldehyde and mono, di, or tri-alkyl substituted benzaldehydes are useful as nucleating agents for polyolefins. Preferred examples claimed within this patent are derived from benzaldehyde and 2,4- dimethylbenzaldehyde or 4-methylbenzaldehyde (p-tolualdehyde). Japanese Patent No. 2[1990]-59832 teaches the preparation and use of pure asymmetric dibenzylidene sorbitol and xylitol systems as gelling agents and nucleating agents. Japanese Patent 7[1995]-286066 discloses the use of asymmetric DBS derivatives derived from 3,4-dimethylbenzaldehyde and various alkyl-substituted or alkoxy-substituted benzaldehydes such as tetralin aldehyde as nucleating agents for polyolefins. Japanese Patent No. 8[1996]-27323 teaches that mixtures of symmetrical DBS systems with organic phosphate salts or amide derivatives provide improved transparency in polyolefins.

Dibenzylidene sorbitol (DBS) is a well known gelling agent for a variety solvent systems as disclosed in U.S. Pat. No. 4,154,816, Roehl et al.; U.S. Pat. No. 4,816,261, Luebbe et al.; and U.S. Pat. No. 4,743,444 to McCall. U.S. Pat. No. 5,609,855 to Oh et al. band W.O. Pat. No. 9219221 to Juneja et al. disclose that di(meta-fluorobenzylidene) sorbitol and di(meta-chlorobenzylidene) sorbitol are extremely useful as gelling agents in the preparation of antiperspirant gel sticks. These two respective DBS systems form effective hard gels and show improved gel stability in the acidic environment of antiperspirant formulations.

DETAILED DESCRIPTION OF THE INVENTION

According to the present invention, a polyolefin plastic composition having improved transparency is provided which comprises a polymer selected from aliphatic polyolefins and copolymers containing at least one aliphatic olefin and one or more ethylenically unsaturated comonomers and at least one nucleating agent conforming to the following Formula (I)

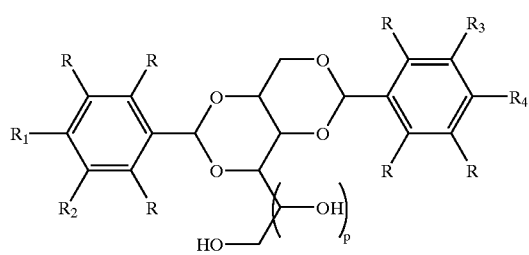

(I)

wherein R is selected from hydrogen, lower alkyl groups containing 1–4 carbon atoms, lower alkoxy groups, and fluorine; $R_1$, and $R_2$, are selected from lower alkyl groups containing 1–4 carbon atoms, lower alkoxy groups, and halogens; $R_3$, and $R_4$ are selected from lower alkyl groups containing 1–4 carbon atoms and which together may form a carbocyclic ring containing up to 6 carbon atoms, lower alkoxy groups, halogens, and hydrogen; with the proviso that only one of $R_1$ and $R_2$ is halogen; and p is 0 or 1.

The individual compounds as defined for Structure (I) are inventive compounds alone as well, broadly stated as asymmetric alditol di-acetal compounds comprising at least two arylidene components wherein one of said benzylidene components at least possesses one halogen pendant group in either the 3- or 4-position and one pendant group selected from lower alkyl and lower alkoxy in the 3- or 4-position.

However, as noted above, the compounds conforming with Structure (I), above, may also be utilized individually within the target polyolefin formulations or combined in some manner and in any proportions as well. More particularly, it is contemplated that reaction product mixtures of isomeric compounds confirming to Structure (I) as well as other dibenzylidene alditol compounds will be formed during production of the desired asymmetric compounds of this invention. It is important to note that the reaction necessary to produce the desired asymmetric diacetals requires the utilization of different benzaldehyde reactants. In such a reaction, invariably different diacetal compounds will be produced. For example, Example 1, below, shows the production of a mixture of 1,3-O-(4-fluoro-3-methylbenzylidene):2,4-O-(3,4-dimethylbenzylidene) sorbitol and 1,3-O-(3,4-dimethylbenzylidene):2,4-O-(4-fluoro-3-methylbenzylidene) sorbitol, 1,3:2,4-bis(3,4-dimethylbenzylidene) sorbitol, and 1,3:2,4-bis(4-fluoro-3-methylbenzylidene) sorbitol simultaneously. Due to the similar solubilities of such DBS compounds (in each instance, not just Example 1), it has been found to be extremely difficult to separate these individual compounds from the reaction product mixture. Such a mixture thus not only includes the desired inventive asymmetric compound or compounds, but such a mixture is an inventive composition as well. Hence, the terms "diacetal compositions", as well as "reaction product mixtures" (as well as their singular forms) are intended to encompass such an inventive mixture including the desired asymmetries.

In order to produce such diacetal compositions (and thus the inventive asymmetric compounds themselves), the starting materials must include the desired alditol (such as D-sorbitol), and at least two different substituted benzaldehydes (or one could be unsubstituted), including arylaldehydes. Generally, as noted above, the molar ratio of alditol to benzaldehyde reactant is at least 1:2 for diacetal formation. In this specific situation of producing asymmetric compounds, the same general molar ratio is followed (with the ability to use more or less of either type of reactant if desired); however, the benzaldehyde component is measured as a total amount of the at least two different benzaldehyde reactant compounds necessary for asymmetric production. Thus, the benzaldehyde component is split into at least two different measurements of the individual reactants utilized. Such a split of amounts can be as disparate as a range of from 1:25 to 25:1 of molar ratios of benzaldehydes, if desired. More likely, and more desired, however, is a range of from 1:5 to 5:1, preferably from 1:4 to 4:1, more preferably from 1:3 to 3:1, still more preferably from 1:2 to 2:1, and most preferably a molar ratio of substantially 1:1.

With such a required reaction of different benzaldehydes and alditol, one of ordinary skill in the art would theoretically expect that approximately 25% yield of each possible compound is realized. However, it appears that the asymmetrics unexpectedly are produced in greater yields (in combination upwards of from about 60 to 80%), well above the expected yield. Such a "reaction product" mixture has been found, unexpectedly, to be useful in providing excellent clarifying, nucleating, etc., properties within the target polyolefin. On the other hand, "physical" mixtures of individual inventive compounds (with other inventive compounds or with other types of DBS clarifiers) may also be followed to produce highly desirable clarity, nucleation, and the like, within target polyolefins. Thus, selected mixtures of from about 25 to 90% of (a) and from about 25 to 90% of another compound [or the same with (b)] are highly effective as well.

It should be appreciated with regard to the structural formulae set forth above that while only the 1,3:2,4 isomer is represented, this structure is provided for convenience only and the invention is not limited to only isomers of the 1,3:2,4 type, but may include any and all other isomers as well so long as the compound contains two aldehyde substitutents on the alditol moiety.

Throughout this specification, the term "asymmetrical" as it pertains to di-acetals of alditols is intended to mean wherein such alditol acetals possess 1,3- and 2,4- acetal linkages derived from different aldehydes.

The diacetals of the present invention are a condensation product of an alditol with halogen-alkyl substituted benzaldehydes and other substituted benzaldehydes. Examples of suitable halogen-alkyl substituted benzaldehydes include 4-fluoro-3-methylbenzaldehyde, 3-fluoro-4-methylbenzaldehyde, 4-fluoro-2,3-dimethylbenzaldehyde, 3-fluoro-2,4-dimethylbenzaldehyde, 2,4-difluoro-3-methylbenzaldehyde, 4-fluoro-3,5-dimethylbenzaldehyde, 3-fluoro-4-methoxy-benzaldehyde, 4-chloro-3-methylbenzaldehyde, 3-chloro-4-methylbenzaldehyde, 4-chloro-2,3-dimethylbenzaldehyde, 3-chloro-2,4-dimethylbenzaldehyde, 3-chloro-4-methoxybenzaldehyde, and 3-chloro-4-methoxy-2-methylbenzaldehyde. Preferred halogen-alkyl substituted benzaldehydes of the present invention include 4-fluoro-3-methylbenaldehyde, 3-fluoro-4-methylbenzaldehyde, 4-fluoro-2,3-dimethylbenzaldehyde, 3-fluoro-2,4-dimethylbenzaldehyde, 4-chloro-3-methylbenzaldehyde, 3-chloro-4-methylbenzaldehyde, 4-chloro-2,3-dimethylbenzaldehyde, and 3-chloro-2,4-dimethylbenzaldehyde. Examples of other aldehydes to be used in conjunction with halogen-alkyl subsituted benzaldehydes include benzaldehyde, 4-methyl benzaldehyde, 4-ethylbenzaldehyde, 4-propylbenzaldehyde, 4-butylbenzaldehyde, 4-fluorobenzaldehyde, 4-chloro-benzaldehyde, 4-bromobenzaldehyde, 3-fluorobenzaldehyde, 3-trifluoromethylbenzaldehyde, 3,4-dimethylbenzaldehyde, 3,5-dimethylbenzaldehyde, 2,4-dimethylbenzaldehyde, 2,3-dimethylbenz-aldehyde, 2,5-dimethylbenzaldehyde, 3,4-difluorobenzaldehyde, 3,4-dichloro-benzaldehyde, 3,4-dibromobenzaldehyde, 2,3,4-trimethylbenzaldehyde, 2,4,6-trimethylbenzaldhyde, 3,4,5-trimethylbenzaldehyde, 5,6,7,8-tetrahydro-2-naphthaidehyde, 3,4-dioxymethylene benzaldehyde, 5-formylindan, 6-formyltetralin, and other halogen-alkyl substituted benzaldehydes.

Typical examples of compounds conforming to Formula (I), above, and which can constitute at least portion the nucleating, agent composition contained in the crystalline resin composition of the invention are 1,3-O-(4-fluoro-3-methylbenzylidene):2,4-O-(3,4-dimethylbenzylidene) sorbitol, 1,3-O-(3,4-dimethylbenzylidene):2,4-O-(4-fluoro-3-methylbenzylidene) sorbitol, 1,3-O-(4-fluoro-3-methylbenzylidene):2,4-O-(3-fluoro-4-methylbenzylidene) sorbitol, 1,3-O-(3-fluoro-4-methylbenzylidene):2,4-O-(4-fluoro-3-methylbenzylidene) sorbitol, 1,3-O-(4-fluoro-3-methylbenzylidene):2,4-O-(4-chlorobenzylidene) sorbitol, 1,3-O-(4-chlorobenzylidene):2,4-O-(4-fluoro-3-methylbenzylidene) sorbitol, 1,3-O-(4-chloro-3-methylbenzylidene):2,4-O-(3-chloro-4-methylbenzylidene) sorbitol, 1,3-O-(3-chloro-4-methylbenzylidene):2,4-O-(4-chloro-3-methylbenzylidene) sorbitol, 1,3-O-(4-fluoro-3-methylbenzylidene):2,4-O-(5',6',7',8'-tetrahydro-2-napthylidene) sorbitol, 1,3-O-(5',6',7',8'-tetrahydronapthylidene):2,4-O-(4-fluoro-3-methylbenzylidene) sorbitol, 1,3-O-(4-Chloro-3-methylbenzylidene)-2,4-O-(5',6',7',8'-tetrahydro-2-napthylidene) sorbitol, 1,3-O-(5',6',7',8'-tetrahydronapthylidene):2,4-O-(4-chloro-3-methylbenzylidene) sorbitol, 1,3-O-(3-bromo-4-ethylbenzylidene):2,4-O-(3,4-dimethylbenzylidene) sorbitol, 1,3-O-(3-bromo-4-isopropylbenzylidene):2,4-O-(3,4-dimethylbenzylidene) sorbitol, 1,3-O-(3-bromo-4-methylbenzylidene):2,4-O-(3,4-dimethylbenzylidene) sorbitol, 1,3-O-(4-chlorobenzylidene):2,4-O-(3-bromo-4-isopropylbenzylidene) sorbitol, and the like.

The compositions of the present invention also include solvent gels containing 0.2% to 10% of the above di-acetals as a gelling agent. Solvents useful herein include, for example lower monohydric alcohols, polyhydric alcohols, and mixtures thereof. Water may be included as part of the solvent. However, the solvent will generally comprise water at levels no greater than 5% by weight of the final composition. Examples of solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol, monomethyl ether, diethylene glycol, monoethylether, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivatives). Examples of such compounds are butyl ether derivatives of polypropylene polyethylene glycol copolymers, such as PPG-5-buteth-7.

These solvents are fully described, for example, in U.S. Pat. No. 4,518,582 to Schamper et al. and European Published Application 107,330 to Luebbe et al. incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, glycerin, dipropylene glycol, tripropylene glycol, triethylene glycol, hexylene gylcol, and mixtures thereof.

Other organic solvents useful herein include aromatics, halogenated aromatics, nitrated aromatics, ketones, amines, nitriles, esters, aldehydes, and mixtures thereof. Examples of solvents which may be utilized in the present invention include xylenes (o, m, and p-substituted), 2-chlorotoluene, fluorobenzene, nitrobenzene, benzonitrile, dimethylsulfoxide (DMSO), N,N-dimethylformamide (DMF), and 1-methyl-2-pyrrolidinone (NMP).

The di-acetals of the present invention may conveniently prepared by a variety of techniques, some of which are known in the art. Generally, such procedures employ the reaction of one mole of D-sorbitol with about 2 moles of aldehyde in the presence of an acid catalyst. The temperature employed in the reaction will vary widely depending upon the characteristics, such as melting point, of the aldehyde or aldehydes employed as a starting material in the reaction. The reaction medium may be an aqueous medium or a non-aqueous medium. One very advantageous method that can be employed to prepare di-acetals of the invention is described in U.S. Pat. No. 3,721,682, to Murai et al. (New Japan Chemical Company Limited), the disclosure of which is hereby incorporated herein by reference. While the disclosure of the patent is limited to benzylidene sorbitols, it has been found that the di-acetals of the present invention may also be conveniently prepared by the method described therein. Additional methods for preparing DBS systems can be found in U.S. Pat. No. 5,731,474 to Scrivens et al., U.S. Pat. No. 4,902,807 to Kobayashi et al. which discloses DBS having an alkyl group or halogen for use as clarifying agents, and U.S. Pat. No. 5,106,999 to Gardlik et al. which discloses the preparation of di(meta-fluorobenzylidene) sorbitol, di(meta-chlorobenzylidene) sorbitol, and di(meta-bromobenzylidene) sorbitol.

Of course, as was noted above, the reaction required to produce the desired asymmetric compounds of this invention comprises reactants of alditol (such as D-sorbitol) and a total amount of at least two different benzaldehydes in a ration of alditol to benzaldehyde of from about 1:4 to about 4:1, preferably from 1:3 to 3:1, and most preferably about 1:2. Again, as noted above, the resultant composition thus comprises the desired asymmetric or asymmetrics, and two other symmetric compounds.

The di-acetals of sorbitol of the present invention prepared by the above techniques may contain a minor or even a major portion of by-product mono-acetal and tri-acetal as impurities (in addition to the aforementioned expected reaction product mixture compounds. Although it may not always be necessary to remove these impurities prior to incorporation of the di-acetal into the polyolefin, it may be desirable to do so and such purification may serve to enhance the transparency of the resin produced thereby. Purification of the di-acetal may be accomplished, for instance, by removal of the tri-acetal impurities by the extraction thereof with a relatively non-polar solvent. By removal of the impurities, the product may be purified so that the amount of di-acetal in the additive composition contains, preferably, though not necessarily, at least about 90 percent and even up to 95 percent of the di-acetal composition or more.

The proportion of di-acetal in the composition of this invention is an amount sufficient to improve the transparency of the composition, generally from about 0.01 to about 2 percent by weight, preferably about 0.1 to about 1 percent by weight, based upon the total weight of the composition may be provided. When the content of the di-acetal composition is less than about 0.01 percent by weight, the resulting composition may not be sufficiently improved in respect to transparency characteristics. When the content of di-acetal composition is increased beyond about 2 percent by weight, no additional advantage can be observed.

The polyolefin polymers of the present invention may include aliphatic polyolefins and copolymers made from at least one aliphatic olefin and one or more ethylenically unsaturated comonomers. Generally, the comonomers, if present, will bed provided in a minor amount, e.g., about 10 percent or less or even about 5 percent or less, based upon the weight of the polyolefin. Such comonomers may serve to assist in clarity improvement of the polyolefin, or they may function to improve other properties of the polymer. Examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as, without limitation, polyethylene, linear low density polyethylene, polypropylene, crystalline ethylenepropylene copolymer, poly(1-butene), polymethylpentene, 1-hexene, 1-octene, and vinyl cyclohexane. The polyolefins of the present invention may be described as basically linear, regular polymers that may optionally contain side chains such as are found, for instance, in conventional, low density polyethylene.

Other polymers that may benefit from the nucleation and clarification properties of the sorbitol acetals of the present invention include polyethylene terephthalate, polybutylene terephthalate, and nylons, among others.

The olefin polymer or copolymer used in the composition of the present invention is crystalline, and the diffraction of light caused by micro crystals contained in it is considered to be responsible for the deterioration of the transparency of the polymer. It is thought that the di-acetal composition functions in the target polyolefin to reduce the size of the microcrystals thereby improving the transparency of the polymer.

The composition of the present invention can be obtained by adding a specific amount of the di-acetal composition directly to the olefin polymer or copolymer, and merely mixing them by an suitable means. Alternatively, a concentrate containing as much as about 20 percent by weight of the di-acetal composition in a polyolefin masterbatch may be prepared and be subsequently mixed with the resin. Furthermore, the inventive alditol derivatives (and other additives) may be present in any type of standard polyolefin additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

Other additives such as a transparent coloring agent or plasticizers (e.g., dioctyl phthalalte, dibutyl phthalate, dioctyl sebacate, mineral oil, or dioctyl adipate), can be added to the composition of the present invention so long as they do not adversely affect the improvement of transparency of the product. It has been found that plasticizers such as those exemplified above may in fact aid in the improvement of the transparency by the di-acetal composition.

With regard to other additives it may also be desirable to employ the di-acetal compositions disclosed above in combination with other conventional additives having known transparency improving effects such as, for instance, para-t-butylbenzoic acid, its salts, low molecular weight waxy polypropylene and the like. It may even be desirable to provide the particular di-acetal composition of the present invention in the polyolefin composition in combination with the previously described dibenzylidene sorbitol additive disclosed in U.S. Pat. Nos. 4,016,118 to Hamada et al., 5,049,605 to Rekers, and the like. In such applications, generally at least about 10 percent, preferably about 25 percent, or even about 50 percent or more of the clarity improving component will be the diacetal compositions of the present invention, with the remainder being comprised of other known clarifying agents, plasticizers, etc.

The compositions of the present invention may be obtained by adding the halogen-alkylbenzylidene sorbitol acetals to the polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

Other additives may also be used in the composition of the present invention, provided they do not interfere with the primary benefits of the invention. It may even be advantageous to premix these additives or similar structures with the inventive nucleating and/or clarifying reaction product mixtures in order to reduce its melting point and thereby enhance dispersion and distribution during melt processing. Of particular interest is the incorporation of the inventive symmetrical compound or compounds with, without limitation to any specific additive nucleators or clarifiers, selected amounts of certain dibenzylidene sorbitol derivatives, including bis(3,4-dimethylbenzylidene) sorbitol (hereinafter DMDBS). As noted below, such a combination provides unexpected haze benefits within target polyolefin (e.g., polypropylene) plastic articles. Such additives are well known to those skilled in the art, and include plasticizers, lubricants, catalyst neutralizers, antioxidants, light stabilizers, colorants, other nucleating agents, and the like. Some of these additives may provide further beneficial property enhancements, including improved aesthetics, easier processing, and improved stability to processing or end use conditions.

In particular, it is contemplated that certain organoleptic improvement additives be added for the purpose of reducing the migration of degraded benzaldehydes from reaching the surface of the desired article. The term "organoleptic improvement additive" is intended to encompass such compounds and formulations as antioxidants (to prevent degradation of both the polyolefin and possibly the target alditol derivatives present within such polyolefin), acid neutralizers (to prevent the ability of appreciable amounts of residual acids from attacking the alditol derivatives), and benzaldehyde scavengers (such as hydrazides, hydrazines, and the like, to prevent the migration of foul tasting and smelling benzaldehydes to the target polyolefin surface). Such compounds and formulations can be added in any amounts in order to provide such organoleptic improvements as needed. However, the amounts should not appreciably affect the haze results for the target polyolefin itself. Thus, lower amounts on the order of from about 20 ppm to about 2,000 ppm of the total polyolefin component are desired.

The compositions of the present invention are suitable as additives to improve the clarity of packaging materials and container materials for cosmetics, food-stuffs, and the like, because they give film, sheet, and other fabricated articles having excellent transparency and physical properties.

PREFERRED EMBODIMENTS OF THE INVENTION

The following non-limiting examples further illustrate the present invention but are not to be construed as limiting the invention as defined in the claims appended hereto. All parts and percents given in these examples are by weight unless otherwise indicated.

EXAMPLE 1

Preparation of Asymmetric 4-Fluoro-3-methyl/3,4-dimethyl DBS

A one liter four-necked cylindrical shaped reaction flask equipped with a Dean-Stark trap, condenser, thermometer, nitrogen inlet, and a mechanical stirrer was charged with 41.62 g of sorbitol (0.2285 mole), 700 mL of cyclohexane, 31.56 g of 4-fluoro-3-methylbenzaldehyde (0.2285 moles), 30.65 g of 3,4-dimethylbenzaldehyde (0.2285 moles), 3.00 g of p-toluenesulfonic acid, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 73.19 g of Asymmetric 4-Fluoro-3-methyl/3,4-Dimethyl [50/50] DBS. The purity was about 95% as judged by gas chromatography. Analyses of the material by gas chromatography/mass spectrometry, $^1$H NMR, and $C^{13}$ NMR (hereinafter "standard analyses") indicated that it consisted of a mixture of 1,3-O-(4-fluoro-3-methylbenzylidene):2,4-O-(3,4-dimethylbenzylidene) sorbitol and 1,3-O-(3,4-dimethylbenzylidene):2,4-O-(4-fluoro-3-methylbenzylidene) sorbitol (49.8%), 1,3:2,4-bis(3,4-dimethylbenzylidene) sorbitol (29.2%), and 1,3:2,4-bis(4-fluoro-3-methylbenzylidene) sorbitol (20.8%). DSC analysis of the solid @20° C./min showed multiple melting transitions at 232.9, 239.0, and 244.1° C.

EXAMPLE 2

Preparation of Asymmetric 4-Fluoro-3-methyl/4-chloro DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 31.85 g of 4-fluoro-3-methylbenzaldehyde (0.2306 moles), 32.41 g of 4-chlorobenzaldehyde (0.2306 moles), 3.00 g of p-toluenesulfonic acid, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 86.39 g of Asymmetric 4-Fluoro-3-methyl/4-Chloro [50/50] DBS. The purity was about 95% as judged by GC. Standard analyses of the material indicated that it consisted of a mixture of 1,3-O-(4-fluoro-3-methylbenzylidene):2,4-O-(4-chlorobenzylidene) sorbitol and 1,3-O-(4-chlorobenzylidene):2,4-O-(4-fluoro-3-methylbenzylidene) sorbitol (53.0%), 1,3:2,4-bis(4-chlorobenzylidene) sorbitol (27.6%), and 1,3:2,4-bis(4-fluoro-3-methylbenzylidene) sorbitol (19.4%). DSC analysis of the solid @20° C./min showed a peak melting transition at 224.6° C.

EXAMPLE 3

Preparation of Asymmetric 4-Fluoro-3-methyl/3-fluoro-4-methyl DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 31.85 g of 4-fluoro-3-methylbenzaldehyde (0.2306 moles), 31.85 g of 3-fluoro-4-methylbenzaldehyde (0.2306 moles), 3.00 g of p-toluenesulfonic acid, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 72.45 g of asymmetric 4-Fluoro-3-methyl/3-Fluoro-4-methyl [50/50] DBS. The purity was about 95% as judged by GC. Standard analyses of the material indicated that it consisted of a mixture of 1,3-O-(4-fluoro-3-methylbenzylidene):2,4-O-(3-fluoro-4-methylbenzylidene) sorbitol and 1,3-O-(3-fluoro-4-methylbenzylidene):2,4-O-(4-fluoro-3-methylbenzylidene) sorbitol (57.8%), 1,3:2,4-bis(3-fluoro-4-methylbenzylidene) sorbitol (31.9%), and 1,3:2,4-bis(4-fluoro-3-methylbenzylidene) sorbitol (10.3%). DSC analysis of the solid @20° C./min showed a peak melting transition at 261.7° C.

EXAMPLE 4

Preparation of Asymmetric 4-Fluoro-3-methyl/benzaldehyde DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 31.85 g of 4-fluoro-3-methylbenzaldehyde (0.2306 moles), 24.47 g of benzaldehyde (0.2306 moles), 3.00 g of p-toluenesulfonic acid, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 60.39 g of asymmetric 4-Fluoro-3-methyl/benzaldehyde [50/50] DBS. The purity was about 95% as judged by GC. Standard analyses of the material indicated that it consisted of a mixture of 1,3-O-(4-fluoro-3-methylbenzylidene):2,4-O-benzylidene sorbitol and 1,3-O-benzylidene:2,4-O-(4-fluoro-3-methylbenzylidene) sorbitol (50.9%), 1,3:2,4-bis(benzylidene) sorbitol (18.2%), and 1,3:2,4-bis(4-fluoro-3-methylbenzylidene) sorbitol (30.8%). DSC analysis of the solid @20° C./min showed multiple melting transitions at 200.9 and 211.2° C.

EXAMPLE 5

Preparation of Asymmetric 4-Fluoro-3-methyl/3-chloro-4-fluoro DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 31.85 g of 4-fluoro-3-methylbenzaldehyde (0.2306 moles), 36.56 g of 3-chloro-4-fluorobenzaldehyde (0.2306 moles), 3.00 g of p-toluenesulfonic acid, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 84.74 g of asymmetric 4-Fluoro-3-methyl/3-Chloro-4-fluoro [50/50] DBS. The purity was about 95% as judged by GC. Standard analyses of the material indicated that it consisted of a mixture of 1,3-O-(4-fluoro-3-methylbenzylidene):2,4-O-(3-chloro-4-fluorobenzylidene) sorbitol and 1,3-O-(3-chloro-4-fluorobenzylidene):2,4-O-(4-fluoro-3-methylbenzylidene) sorbitol (52.8%), 1,3:2,4-bis(3-chloro-4-fluorobenzylidene) sorbitol (22.4%), and 1,3:2,4-bis(4-fluoro-3-methylbenzylidene) sorbitol (24.7%). DSC analysis of the solid @20° C./min showed a peak melting transition at 238.9° C.

EXAMPLE 6

Preparation of Asymmetric 4-Chloro-3-methyl/3-chloro-4-methyl DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 53.46 g of 4-chloro-3-methylbenzaldehyde (0.3458 moles), 17.82 g of 3-chloro-4-methylbenzaldehyde (0.1152 moles), 3.00 g of p-toluenesulfonic acid, and 210 mL of methanol. The reaction was stirred and heated under reflux with removal of water through the Dean Stark trap. The reaction becomes very thick and additional solvent is added as needed. After about six hours, the reaction is cooled, neutralized with potassium hydroxide, and filtered. The wet cake is washed thoroughly with water and cyclohexane, dried in a vacuum oven at 110° C. to give 85.31 g of asymmetric 4-Chloro-3-methyl/3-Chloro-4-methyl [75/25] DBS. The purity was about 95% as judged by GC. Standard analyses of the material indicated that it consisted of a mixture of 1,3-O-(4-chloro-3-methylbenzylidene):2,4-O-(3-chloro-4-methylbenzylidene) sorbitol and 1,3-O-(3-chloro-4-methylbenzylidene):2,4-O-(4-chloro-3-methylbenzylidene) sorbitol (38.2%), 1,3:2,4-bis(3-chloro-4-methylbenzylidene) sorbitol (5.3%), and 1,3:2,4-bis(4-chloro-3-methylbenzylidene) sorbitol (56.6%). DSC analysis of the solid (20° C./min showed a peak melting transition at 267.4° C.

EXAMPLE 7

Preparation of Asymmetric 3-Bromo-4-methyl/3,4-dimethyl DBS

To an open reactor equipped with a mechanical stirrer was charged with 25 g of sorbitol (0.14 mole), concentrated HCl (34.8 g), and 0.38 g of dodecylbenzene sulfonate were charged to an open reaction vessel and stirred. After five minutes, 32 g of ground 2-(3-bromo-4-ethylphenyl)-1,3-dioxane (0.12 mol) and 3,4-dimethylbenzaldehyde (21 g; 0.16 mol) were mixed together with the initial formulation. After 8 hours of stirred reaction, 200 mL of cold water and KOH (72 g) were added. The resultant solids were then filtered and washed in basic water (800 mL with small amounts of KOH), then hot methanol (800 mL), then room temperature toluene (500 mL). Upon the addition of deionized water (400 mL) a white precipitate formed which was then dried by suction filtration and washed by stirring in methanol (800 mL), yielding 3-bromo-4-ethyl/3,4-dimethyl DBS mixtures as a light tan solid. Standard analyses of the material indicated that it consisted of a mixture of bis(3-bromo-4-ethylbenzylidene) sorbitol (10.3%), bis(3,4-dimethylbenzylidene) sorbitol (34.8%), and the remainder an asymmetric mixture of 1,3-O-(3-bromo-4-ethylbenzylidene):2,4-O-(3,4-dimethylbenzylidene) sorbitol and 1,3-O-(3,4-dimethylbenzylidene):2,4-O-(3-bromo-4-ethylbenzylidene) sorbitol. A melting transition was observed at 256.7–257.5° C. when heated at 3° C./min on an Electrothermal 9300 Melting Point Apparatus.

EXAMPLE 8

Preparation of Asymmetric 3-Bromo-4-isopropyl/3,4-dimethyl DBS

To an open reactor equipped with a mechanical stirrer was charged with 20.1 g of sorbitol (0.137 mole), concentrated HCl (34.8 g), and 0.34 g of dodecylbenzene sulfonate were charged to an open reaction vessel and stirred. After five minutes, 33.3 g of ground 2-(3-bromo-4-isopropylphenyl)-1,3-dioxane (0.117 mol) and 3,4-dimethylbenzaldehyde (21.0 g; 0.157 mol) were mixed together with the initial formulation. After 8 hours of stirred reaction, 200 mL of cold water and KOH (72 g) were added. The resultant solids were then filtered and washed in basic water (800 mL with small amounts of KOH), then boiling methanol (800 mL), yielding an asymmetric mixture of 3-bromo-4-isopropyl/3,4-dimethyl DBS as a light tan solid (6.9 g), exhibiting a melting point of 230.6–236.3° C. Standard analyses of the material indicated that it consisted of a mixture of bis(3-bromo-4-isopropylbenzylidene) sorbitol (1.8%), bis(3,4-dimethylbenzylidene) sorbitol (65.1%), and the remainder an asymmetric mixture of 1,3-O-(3-bromo-4-isopropylbenzylidene):2,4-O-(3,4-dimethylbenzylidene) sorbitol and 1,3-O-(3,4-dimethylbenzylidene):2,4-O-(3-bromo-4-isopropylbenzylidene) sorbitol.

EXAMPLE 9

Preparation of Asymmetric 3-Bromo-4-methyl/3,4-dimethyl DBS

To an open reactor equipped with a mechanical stirrer was charged with 25 g of sorbitol (0.14 mole), concentrated HCl (34.8 g), and 0.38 g of dodecylbenzene sulfonate were charged to an open reaction vessel and stirred. After five minutes, 30.3 g of ground 2-(3-bromo-4-methylphenyl)-1,3-dioxane (0.117 mol) and 21 g (0.157 mol) of 3,4-dimethylbenzaldehyde were mixed together with the initial formulation. After 8 hours of stirred reaction, 200 mL of cold water and KOH (72 g) were added. The resultant solids were then filtered and washed in basic water (800 mL with small amounts of KOH), then hot methanol (800 mL), then room temperature toluene (500 mL). The resultant solution was then poured into 400 mL of deionized water, thus precipitating a white solid which was then collected, dried by suction filtration, and washed by stirring in methanol (2 L), yielding 3-bromo-4-methyl/3,4-dimethyl DBS as a light tan solid. Standard analyses of the material indicated that it consisted of a mixture of bis(3-bromo-4-methylbenzylidene) sorbitol (15.2%), bis(3,4-dimethylbenzylidene) sorbitol (24.5%), and the remainder an asymmetric mixture of 1,3-O-(3-bromo-4-methylbenzylidene):2,4-O-(3,4-dimethylbenzylidene) sorbitol and 1,3-O-(3,4-dimethylbenzlidene):2,4-O-(3-bromo-4-methylbenzylidene) sorbitol. A melting transition was observed at 271.9–274.5° C. when heated at 3° C./min on an Electrothermal 9300 Melting Point Apparatus.

EXAMPLE 10

Preparation of 4-Chloro/3-bromo-4-isopropyl asymmetric DBS

To an open reactor equipped with a mechanical stirrer was charged with 12.6 g of sorbitol (0.0692 mole), concentrated HCl (15 mL), 7.8 g of water, 15.7 g of 3-bromo-4-isopropylbenzylaldehyde (0.0692 mol), 9.69 g of 4-chlorobenzaldehyde (0.069 mol), and 0.2 g of dodecylbenzene sulfonate and the reactants were stirred together for 24 hours. A white solid precipitate formed during the reaction and was neutralized after the reaction was complete with a solution of KOH (10 g) in water (250 mL). The resultant solids were then collected by filtration and washed by stirring in boiling water then boiling cyclohexane to provide a 4-chloro/3-bromo-4-isopropyl asymmetric DBS mixture as a white powder exhibiting a melting transition of 212.5–218.9°. Standard analyses of the material indicated that it consisted of a mixture of bis(3-bromo-4-isopropylbenzylidene) sorbitol (14%), bis(4-chlorobenzylidene) sorbitol (45%), and the remainder an asymmetric mixture of 1,3-O-(3-bromo-4-isopropylbenzylidene):2,4-O-(4-chlorobenzylidene) sorbitol and 1,3-O-(4-chlorobenzylidene):2,4-O-(3-bromo-4-isopropylbenzylidene) sorbitol.

Production of Polyolefin Articles and Testing Thereof

One kilogram batches of target polypropylene were produced in accordance with the following table:

| POLYPROPYLENE COMPOSITION TABLE | |
|---|---|
| Component | Amount |
| Polypropylene random copolymer flake (3% ethylene) (MFI = 12) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Diacetal (and diacetal compositions) | as noted |

The base resin (random copolymer, hereinafter "RCP") and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The barrel molder was set at a temperature anywhere between 190 and 260° C., with a range of 190 to 240° C. preferred, most preferably from about 200 to 230° C. The plaques had dimensions of about 51 mm×76 mm×1.27 mm, and were made in a mold having a mirror finish. The mold cooling circulating water was controlled at a temperature of about 25° C.

The same basic procedures were followed for the production of plaques of HP and LLDPE plastics but with the following composition:

| LINEAR LOW DENSITY POLYETHYLENE COMPOSITION TABLE | |
|---|---|
| Component | Amount |
| Dowlex ® 2517 Linear Low Density Polyethylene (with Antioxidants and Acid scavengers already supplied) | 1000 g |
| Sodium Stearate | 500 ppm |
| Inventive Diacetal (and diacetal compositions) | as noted |

The haze values were measured by ASTM Standard Test Method D1003-61 "Standard Test Method for Haze and Luminous Transmittance of Transparent Plastics" using a BYK Gardner XL-211 Hazemeter. Nucleation capabilities were measured as polymer recrystallization temperatures (which indicate the rate of polymer formation provided by the presence of the nucleating additive) by melting the target plaques, cooling the plaques at a rate of about 20° C./minute, and recording the temperature at which polymer re-formation occurs. Control plaques without alditol additives were produced for comparative purposes for some or all of the above-noted measurements. An asterisk (*) denotes no measurements were taken.

EXPERIMENTAL TABLE 1
Polyolefin Plaques and Characteristics Thereof

| Test Plaque No. | Additive (Example # from above) | Conc. (%) | Haze (%) | Resin Grade | Part Thick. (mil) | Polym. Recryst. Temp. (° C.) |
|---|---|---|---|---|---|---|
| 1 | None | — | 55.8 | RCP | 50 | 96.1 |
| 2 | 1 | .15 | 15.7 | RCP | 50 | * |
| 3 | 1 | .20 | 8.6 | RCP | 50 | * |
| 4 | 1 | .25 | 6.8 | RCP | 50 | 112.3 |
| 5 | 1 | .35 | 6.4 | RCP | 50 | 112.5 |
| 6 | None | — | 95.2 | RCP | 100 | 94.3 |
| 7 | 1 | .15 | 44.6 | RCP | 100 | * |
| 8 | 1 | .20 | 33.9 | RCP | 100 | * |
| 9 | 1 | .25 | 31.1 | RCP | 100 | * |
| 10 | 1 | .35 | 29.1 | RCP | 100 | * |
| 11 | 2 | .25 | 9.7 | RCP | 50 | 114.5 |
| 12 | 2 | .35 | 8.0 | RCP | 50 | 115.3 |
| 13 | 2 | .50 | 7.3 | RCP | 50 | 115.7 |
| 14 | 3 | .25 | 7.5 | RCP | 50 | 113.9 |
| 15 | 3 | .35 | 6.6 | RCP | 50 | 113.5 |
| 16 | 3 | .5 | 6.3 | RCP | 50 | * |
| 17 | 6 | .15 | 25.0 | RCP | 50 | 108.5 |
| 18 | 6 | .25 | 9.4 | RCP | 50 | 111.8 |
| 19 | 6 | .35 | 6.1 | RCP | 50 | 112.3 |
| 20 | 6 | .50 | 5.4 | RCP | 50 | 112.6 |
| 21 | None | — | 90.1 | LLDPE | 50 | 99.6 |
| 22 | 2 | .25 | 44.6 | LLDPE | 50 | |
| 23 | 2 | .35 | 47.2 | LLDPE | 50 | 108.9 |
| 24 | 3 | .25 | 51.0 | LLDPE | 50 | |
| 25 | 3 | .35 | 51.7 | LLDPE | 50 | 108.4 |
| 26 | 4 | .20 | 86.1 | LLDPE | 50 | * |
| 27 | 4 | .25 | 59.6 | LLDPE | 50 | * |
| 28 | 4 | .35 | 47.9 | LLDPE | 50 | 106.1 |
| 29 | 5 | .20 | 81.7 | LLDPE | 50 | * |
| 30 | 5 | .25 | 57.8 | LLDPE | 50 | * |
| 31 | 5 | .35 | 46.8 | LLDPE | 50 | * |
| 32 | 6 | .25 | 44.3 | LLDPE | 50 | * |
| 33 | 6 | .35 | 48.6 | LLDPE | 50 | * |
| 34 | 6 | .45 | 49.2 | LLDPE | 50 | * |
| 35 | 7 | .3 | 12.9 | RCP | 50 | * |
| 36 | 7 | .4 | 8.6 | RCP | 50 | 111.3 |
| 37 | 8 | .3 | 11.3 | RCP | 50 | * |
| 38 | 8 | .4 | 9.2 | RCP | 50 | 111.1 |
| 39 | 9 | .3 | 11.1 | RCP | 50 | * |
| 40 | 9 | .4 | 9.6 | RCP | 50 | 111.7 |
| 41 | 10 | .35 | 23.8 | RCP | 50 | 105.0 |

Thus, the inventive asymmetric halogenated and alkylated alditol derivatives provided much improved optical and nucleation characteristics within the target thermoplastics as compared with the control.

Formation and Testing

Solid gels were also produced comprising the inventive alditol derivatives through recognized, simple methods. In particular, specific organic solvents were combined with additives in certain concentrations and mixed thoroughly. The resultant mixture was heated to a temperature between about 170° F. (77° C.) and 300° F. (149° C.), as indicated below, under agitation for between 5 and 120 minutes. The resultant solution was then poured into a mold to produce a gel stick. The solvents listed below are not intended to be exhaustive as to the potential types which may be utilized to form gels with the inventive alditol derivatives, and thus are merely listed as preferred solvents for such purposes. The examples below were analyzed empirically and by touch to determine if a gel actually formed and the hardness properties as well as any formed gels.

EXPERIMENTAL TABLE 2

| Ex. No. | Solvent | Additive - from Example # above | DBS Conc. (weight %) | Gel Formation (Y/N) | Gel Character (Hard/Soft) |
|---|---|---|---|---|---|
| 42 | 1,2-Propanediol | 2 | 1 | Y | H |
| 43 | 1,2-Propanediol | 2 | 3 | Y | H |
| 44 | 1,3-Propanediol | 2 | 1 | Y | H |
| 45 | 1,3-Propanediol | 2 | 3 | Y | H |
| 46 | 2-Chlorotoluene | 2 | 1 | Y | H |
| 47 | 2-Chlorotoluene | 2 | 3 | Y | H |
| 48 | Benzonitrile | 2 | 1 | Y | H |
| 49 | Benzonitrile | 2 | 3 | Y | H |
| 50 | 1,2-Propanediol | 3 | 1 | Y | S |
| 51 | 1,2-Propanediol | 3 | 3 | Y | S |
| 52 | 1,3-Propanediol | 3 | 1 | Y | H |
| 53 | 1,3-Propanediol | 3 | 3 | Y | H |
| 54 | 2-Chlorotoluene | 3 | 1 | Y | S |
| 55 | 2-Chlorotoluene | 3 | 3 | Y | H |
| 56 | Benzonitrile | 3 | 1 | Y | S |
| 57 | Benzonitrile | 3 | 3 | Y | H |
| 58 | 1,2-Propanediol | 4 | 1 | Y | S |
| 59 | 1,2-Propanediol | 4 | 3 | Y | H |
| 60 | 1,3-Propanediol | 4 | 1 | Y | S |
| 61 | 1,3-Propanediol | 4 | 3 | Y | H |
| 62 | 2-Chlorotoluene | 4 | 1 | Y | S |
| 63 | 2-Chlorotoluene | 4 | 3 | Y | H |
| 64 | Benzonitrile | 4 | 1 | Y | S |
| 65 | Benzonitrile | 4 | 3 | Y | H |
| 66 | 1,2-Propanediol | 6 | 1 | Y | S |
| 67 | 1,2-Propanediol | 6 | 3 | Y | H |
| 68 | 1,3-Propandiol | 6 | 1 | Y | S |
| 69 | 1,3-Propanediol | 6 | 3 | Y | H |
| 70 | 2-Chlorotoluene | 6 | 1 | Y | S |
| 71 | 2-Chlorotoluene | 6 | 3 | Y | H |
| 72 | Benzonitrile | 6 | 1 | Y | S |
| 73 | Benzonitrile | 6 | 3 | Y | H |

Thus, the inventive asymmetric halogenated and alkylated alditol derivatives provide excellent gelling capabilities for solvents, depending on their concentration within the target solvents.

There are, of course, many alternative embodiments and modifications of the present invention which are to be included within the spirit and scope of the following claims.

What is claimed is:

1. An asymmetric alditol di-acetal comprising at least two arylidene components wherein one of said arylidene components at least possesses one halogen pendant group in either the 3- or 4-position and one pendant group selected from lower alkyl and lower alkoxy in either the 3- or 4-position.

2. An asymmetric compound conforming to the structure of Formula (I)

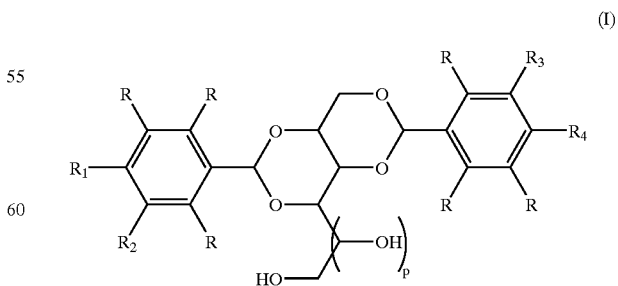

(I)

wherein R is selected from hydrogen, lower alkyl groups containing 1–4 carbon atoms, lower alkoxy groups, and fluorine; $R_1$ and $R_2$, are selected from lower alkyl groups containing 1–4 carbon atoms, lower alkoxy groups, and halogens; $R_3$ and $R_4$ are selected from lower alkyl groups containing 1–4 carbon atoms and which together may form a carbocyclic ring containing up to 6 carbon atoms, lower alkoxy groups, halogens, and hydrogen; with the proviso that only one of $R_1$ and $R_2$ is halogen; and p is 0 or 1.

3. A polyolefin plastic composition comprising at least one compound defined by claim 1.

4. A polyolefin plastic composition comprising at least one compound defined by claim 2.

5. A polyolefin plastic composition having improved transparency, which comprises at least one homopolymer of an aliphatic monoolefin or a copolymer containing an aliphatic monoolefin, said monoolefin containing from 2 to about 6 carbon atoms having an average molecular weight of from about 10,000 to about 500,000 and one or more ethylenically unsaturated aliphatic comonomers, said copolymer having been made by polymerizing said monoolefin with said comonomer; and at least one asymmetric diacetal selected from the group conforming with the structure of Formula (I)

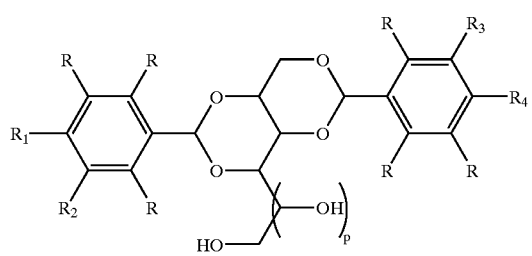

(I)

wherein R is selected from hydrogen, lower alkyl groups containing 1–4 carbon atoms, lower alkoxy groups, and fluorine; $R_1$ and $R_2$, are selected from lower alkyl groups containing 1–4 carbon atoms, lower alkoxy groups, and halogens; $R_3$ and $R_4$ are selected from lower alkyl groups containing 1–4 carbon atoms and which together may form a carbocyclic ring containing up to 6 carbon atoms, lower alkoxy groups, halogens, and hydrogen; with the proviso that only one of $R_1$ and $R_2$ is halogen; and p is 0 or 1.

6. The composition of claim 4, wherein said polyolefin comprises at least one aliphatic monoolefin selected from the group consisting of ethylene, propylene, copolymers of ethylene and propylene, vinyl cyclohexane, methylpentene, 1-hexene, 1-octene, and 1-butene.

7. The composition of claim 4, which further includes at least one plasticizer selected from the group consisting of dioctyl phthalate, dibutyl phthalate, dioctyl sebacate, mineral oil, and dioctyl adipate.

8. The polyolefin plastic composition of claim 4 wherein the proportion of the total amount of diacetal compounds within said polyolefin composition is from about 0.01 to about 2 percent by weight based upon the total weight of the composition.

9. The composition of claim 6, wherein the aliphatic monoolefin is selected from the group consisting of ethylene, propylene, 1-butene, vinyl cyclohexane, and methylpentene.

10. A solid gelled composition comprising at least one asymmetric gelling agent compound conforming to the structure of Formula (I)

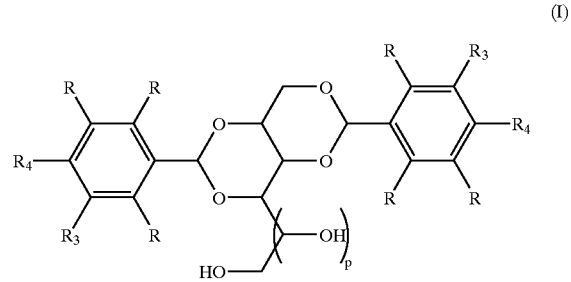

(I)

wherein R is selected from hydrogen, lower alkyl groups containing 1–4 carbon atoms, lower alkoxy groups, and fluorine; $R_1$, and $R_2$, are selected from lower alkyl groups containing 1–4 carbon atoms, lower alkoxy groups, and halogens; $R_3$ and $R_4$ are selected from lower alkyl groups containing 1–4 carbon atoms and which together may form a carbocyclic ring containing up to 6 carbon atoms, lower alkoxy groups, halogens, and hydrogen; with the proviso that only one of $R_1$ and $R_2$ is fluorine or chlorine; and p is 0 or 1; and a solvent for said gelling agent.

11. A solid gel according to claim 9 wherein the solvent is selected from the group consisting of monohydric alcohols, polyhydric alcohols, propylene carbonate, propylene glycol, dipropylene glycol, DMSO, DMF, NMP, water, and mixtures thereof.

12. A solid gel according to claim 10 wherein the solvent is selected from the group consisting of propylene carbonate, methanol, ethanol, n-propanol, n-butanol, 2-methoxyethanol, 2-ethoxyethanol, ethylene glycol, 1,2-propylene glycol, 1,3-propylene glycol, 1,4-butylene glycol, 1,2-butylene glycol, diethylene glycol, isopropanol, isobutanol, monomethyl ether, diethylene glycol monoethyl ether, 1,3-butylene glycol, 2,3-butylene glycol, dipropylene glycol, 2,4-dihydroxy-2-methylpentane, and mixtures thereof.

13. A solid gel according to claim 9 wherein the solvent is selected from aromatics, halogenated aromatics, nitrated aromatics, ketones, amines, nitrites, esters, aldehydes, and mixtures thereof.

14. A reaction product mixture comprising at least two isomers conforming to Formula (I) of claim 1 and at least one other reaction product wherein said at least one other reaction product is a symmetrical alditol compound.

15. A reaction product mixture comprising at least two isomers conforming to Formula (I) of claim 2 and at least one other reaction product wherein said at least one other reaction product is a symmetrical alditol compound.

* * * * *